(12) United States Patent
Luesch et al.

(10) Patent No.: US 9,051,350 B2
(45) Date of Patent: Jun. 9, 2015

US009051350B2

(54) MACROCYCLIC ANTIPROLIFERATION AGENTS AND METHODS OF TREATMENT

(75) Inventors: Hendrik Luesch, Gainesville, FL (US); Valerie J. Paul, Fort Pierce, FL (US); Jason C. Kwan, Salt Lake City, UT (US)

(73) Assignees: University of Florida Research Foundation, Inc., Gainesville, FL (US); Smithsonian Institution, Washington, DC (US)

( * ) Notice: Subject to any disclaimer, the term of this patent is extended or adjusted under 35 U.S.C. 154(b) by 1333 days.

(21) Appl. No.: 12/863,404

(22) PCT Filed: Jan. 15, 2009

(86) PCT No.: PCT/US2009/000395
§ 371 (c)(1),
(2), (4) Date: Apr. 28, 2011

(87) PCT Pub. No.: WO2009/091618
PCT Pub. Date: Jul. 23, 2009

(65) Prior Publication Data
US 2011/0195914 A1    Aug. 11, 2011

Related U.S. Application Data

(60) Provisional application No. 61/011,335, filed on Jan. 16, 2008.

(51) Int. Cl.
*A61K 38/12* (2006.01)
*C07K 5/062* (2006.01)
*A61K 38/00* (2006.01)

(52) U.S. Cl.
CPC ............. *C07K 5/06026* (2013.01); *A61K 38/00* (2013.01)

(58) Field of Classification Search
CPC ..................... A61K 38/00; C07K 5/06026
See application file for complete search history.

(56) References Cited

FOREIGN PATENT DOCUMENTS

WO    WO 2007064691 A1 *  6/2007

OTHER PUBLICATIONS

Kwan et al., Org. Lett., 2008, vol. 10, No. 5, 789-792.*
Kuffner et al., Mar. Ecol. Prog. Ser., 2006, 323: 107-117.*
Kwan et al., Org. Lett., 2008, vol. 10, No. 5, 789-792, also in the ISR of the ISA dated Jul. 16, 2010.*
International Search Report dated May 29, 2009, corresponding to PCT/US2009/000395.
Written Opinion of the International Searching Authority, based on PCT/US2009/000395.
Matthew S et al., "Lyngbyastatin 4, a dolastatin 13 analogue with elastase and chymotrypsin inhibitory activity from the marine cyanobacterium *Lyngbya confervoides*", J Nat Prod. Jan. 2007; 70(1):124-7.
Taori K et al, "Lyngbyastatins 5-7, potent elastase inhibitors from *Floridian* marine cyanobacteria", *Lyngbya* spp, J Nat Prod. Oct. 2007;70(10):1593-600. Epub Oct. 3, 2007.
Kwan JC et al., "Total structure determination of grassypeptolide, a new marine cyanobacterial cytotoxin", Org Lett. Mar. 6, 2008;10(5):789-92. Epub Jan. 26, 2008.

* cited by examiner

*Primary Examiner* — Marcela M Cordero Garcia
*Assistant Examiner* — Kaipeen Yang
(74) *Attorney, Agent, or Firm* — Locke Lord LLP; Jeffrey D. Hsi

(57) ABSTRACT

The instant invention describes macrocyclic compounds having antiproliferation activity, and methods of treating disorders such as cancer, tumors and cell proliferation related disorders.

5 Claims, 14 Drawing Sheets

ROESY Spectrum of Grassypeptolide (1) in DMSO-$d_6$ (600 MHz)

MACROCYCLIC ANTIPROLIFERATION AGENTS AND METHODS OF TREATMENT

CROSS-REFERENCE TO RELATED APPLICATIONS

This application is the U.S. national phase application, pursuant to 35 U.S.C. §371, of PCT International Application No. PCT/US2009/000395, filed Jan. 15, 2009, designating the United States and published in English, which claims priority to U.S. provisional patent application Ser. No. 61/011,335, filed Jan. 16, 2008, the entire contents of the aforementioned patent applications are incorporated herein by this reference.

STATEMENT OF RIGHTS TO INVENTIONS MADE UNDER FEDERALLY SPONSORED RESEARCH

This work was supported in part by a NOAA, Office of Sea Grant, U.S Department of Commerce Grant No. NA06OAR4170014. The government has certain rights in the invention.

BACKGROUND

The identification of new pharmacophores is of paramount biomedical importance and natural products have recently been regaining attention for this endeavor. Koehn, F. E.; Carter, G. T. *Nat. Rev. Drug Discov.* 2005, 4, 206-220; Paterson, I.; Anderson, E. A. *Science* 2005, 310, 451-453. This renaissance is closely tied to the successful exploitation of the marine environment which harbors unmatched biodiversity that is presumably concomitant with chemical diversity. Fenical, W.; Jensen, P. R. *Nat. Chem. Biol.* 2006, 2, 666-673. In particular, marine cyanobacteria are prolific producers of bioactive secondary metabolites (Gerwick, W. H.; Tan, L. T.; Sitachitta, N. *Alkaloids Chem. Biol.* 2001, 57, 75-184), many of which are modified peptides or peptide-polyketide hybrids with promising antitumor activities, such as dolastatin 10 (Luesch, H.; Moore, R. E.; Paul, V. J.; Mooberry, S. L.; Corbett, T. H. *J. Nat. Prod.* 2001, 64, 907-910), curacin A (Gerwick, W. H.; Proteau, P. J.; Nagle, D. G.; Hamel, E.; Blokhin, A.; Slate, D. L. *J. Org. Chem.* 1994, 59, 1243-1245; Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62-76), and apratoxin A (Luesch, H.; Yoshida, W. Y.; Moore, R. E.; Paul, V. J.; Corbett, T. H. *J. Am. Chem. Soc.* 2001, 123, 5418-5423; Luesch, H.; Chanda, S. K.; Raya, M. R.; DeJesus, P. D.; Orth, A. P.; Walker, J. R.; Izpisúa Belmonte, J. C.; Schultz, P. G. *Nat. Chem. Biol.* 2006, 2, 158-167). As a result of ongoing investigations to identify new drug leads from cyanobacteria in Florida, described here is the structure determination and preliminary biological characterization of a marine cyanobacterial metabolite with novel chemical scaffold and antiproliferative activity. These findings provide new alternatives to address unmet needs in the treatment of proliferation diseases and disorders.

Described here is the cytotoxicity-guided isolation of a new cytotoxic depsipeptide, grassypeptolide (1), from an extract of *L. confervoides* collected in the Florida Keys. This cyanobacterium was of interest because it inhibited settlement of coral larvae (*Porites asteroides*) and reduced survival of coral recruits.[1] Grassypeptolide (1) contains some unusual residues, such as the β-amino acid 2-methyl-3-aminobutyric acid (Maba, C1-5) and 2-aminobutyric acid (Aba, C20-23).

Until now, the Aba unit had precedence only in sponge metabolites,[2] whereas the Maba unit was found in one other cyanobacterial compound, guineamide B.[3] Additionally, compound 1 consists of an unusually high number of D-amino acid units. The tandem thiazoline rings flanking the D-Aba derived moiety are reminiscent of the lissoclinamides and the patellamides, which are cyclic peptides containing up to four cysteine- and serine-derived cyclocondensation products and which tend to contain D-amino acids.[4,5] Lissoclinamide 7,[4] closest related to 1 and the most cytotoxic of the series, has two thiazoline rings with the same arrangement and stereoconfiguration as 1, yet the macrocycle is only 21-membered in Lissoclinamide 7 as opposed to 31-membered in 1. Although both the lissoclinamides and the patellamides were originally isolated from the ascidian *Lissoclinum patella*, the biosynthetic gene cluster for patellamides A and C was recently found in the obligate symbiotic cyanobacterium *Prochloron didemni*.[5] Remarkably, these compounds are synthesized ribosomally, rather than by nonribosomal peptide synthetases (NRPS).[5] Grassypeptolide (1) is the first reported compound with tandem thiazoline rings in the depicted arrangement to be produced by an independently living cyanobacterium.

[1] Kuffner, I. B.; Walters, L. J.; Becerro, M. A.; Paul, V. J.; Ritson-Williams, R.; Beach, K. S. *Mar. Ecol. Prog. Ser.* 2006, 323, 107-117.

[2] (a) Fusetani, N.; Sugawara, T.; Matsunaga, S.; Hirota, H. *J. Am. Chem. Soc.* 1991, 113, 7811-7812. (b) Kobayashi, J.; Itagaki, F.; Shigemori, H.; Ishibashi, M.; Takahashi, K.; Ogura, M.; Nagasawa, S.; Nakamura, T.; Hirota, H.; Ohta, T.; Nozoe, S. *J. Am. Chem. Soc.* 1991, 113, 7812-7813. (c) Nakao, Y.; Fujita, M.; Warabi, K.; Matsunaga, S.; Fusetani, N. *J. Am. Chem. Soc.* 2000, 122, 10462-10463.

[3] Tan, L. T.; Sitachitta, N.; Gerwick, W. H. *J. Nat. Prod.* 2003, 66, 764-771.

[4] Wipf, P.; Fritch, P. C.; Geib, S. J.; Sefler, A. M. *J. Am. Chem. Soc.* 1998, 120, 4105-4112.

[5] (a) Schmidt, E. W.; Nelson, J. T.; Rasko, D. A.; Sudek, S.; Eisen, J. A.; Haygood, M. G.; Ravel, J. *Proc. Natl. Acad. Sci. USA* 2005, 102, 7315-7320. (b) Long, P. F.; Dunlap, W. C.; Battershill, C. N.; Jaspars, M. *ChemBioChem* 2005, 6, 1760-1765.

BRIEF SUMMARY OF THE INVENTION

The invention is directed towards macrocyclic compounds, methods of modulating proliferation activity, and methods of treating proliferation disease and disorders.

In one embodiment, the invention provides a compound according to Formula I:

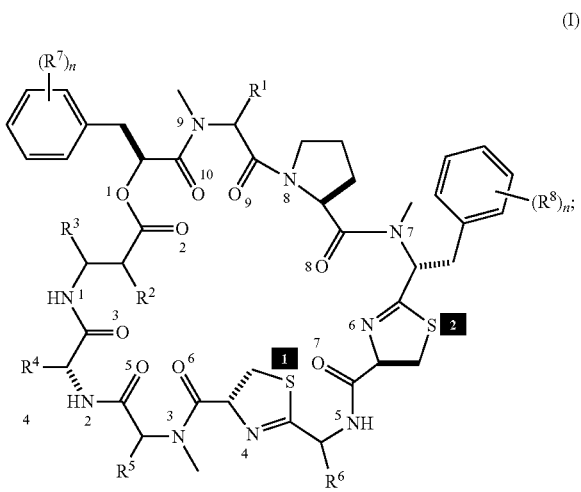

wherein:
each $R^1$ is independently H, or alkyl or aryl, each optionally substituted;
each $R^2$ is independently H, or alkyl or aryl, each optionally substituted;
each $R^3$ is independently H, or alkyl or aryl, each optionally substituted;
each $R^4$ is independently H, or alkyl or aryl, each optionally substituted;
each $R^5$ is independently H, or alkyl or aryl, each optionally substituted;
each $R^6$ is independently H, or alkyl or aryl, each optionally substituted;
each $R^7$ is independently H, or alkyl, hydroxyl, alkoxy, halo, cyano, nitro, mercapto, thioalkoxy, alkoxycarbonyl, carboxyl, amino, mono- or di-alkylamino, or amido, each optionally substituted;
each $R^8$ is independently H, or alkyl, hydroxyl, alkoxy, halo, cyano, nitro, mercapto, thioalkoxy, alkoxycarbonyl, carboxyl, amino, mono- or di-alkylamino, or amido, each optionally substituted;
each n is independently 1, 2, 3 or 4;
and pharmaceutically acceptable salts, solvates, or hydrates thereof.

Other embodiments include a compound of any of the formulae herein, wherein the compound is any of Compounds 1-2 in Table A; or wherein the compound is grassypeptolide (1).

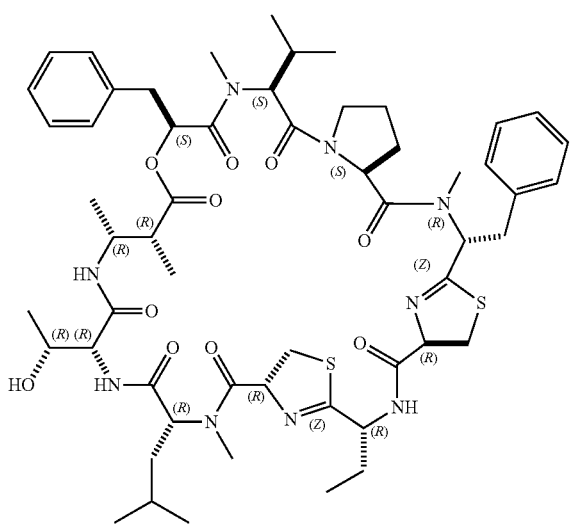

1

In certain instances, the compounds of the invention are selected from the following of Formula (I) having the structure:

TABLE A

| Cmpd No. | $R^1$ | $R^2$ | $R^3$ | $R^4$ | $R^5$ | $R^6$ |
|---|---|---|---|---|---|---|
| 1 | i-Pr | Me | Me | CH$_3$CH(OH)— | i-Bu | Et |
| 2 | i-Pr | H | Me | CH$_3$CH(OH)— | i-Bu | Et |

In another aspect, the invention provides a pharmaceutical composition comprising the compound of formula I and a pharmaceutically acceptable carrier.

In other aspects, the invention provides a method of modulating the proliferation activity in a subject, comprising contacting the subject with a compound of formula I, in an amount and under conditions sufficient to modulate proliferation activity.

In one aspect, the invention provides a method of treating a subject suffering from or susceptible to a proliferation related disorder or disease, comprising administering to the subject an effective amount of a compound or pharmaceutical composition of formula I.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of formula I, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of formula I, such that cell proliferation in said subject is modulated (e.g., down regulated). In another aspect, the compounds delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., Formula I), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

BRIEF DESCRIPTION OF THE DRAWINGS

The present invention is further described below with reference to the following non-limiting examples and with reference to the following figures, in which.

DETAILED DESCRIPTION

Definitions

Figure 1:
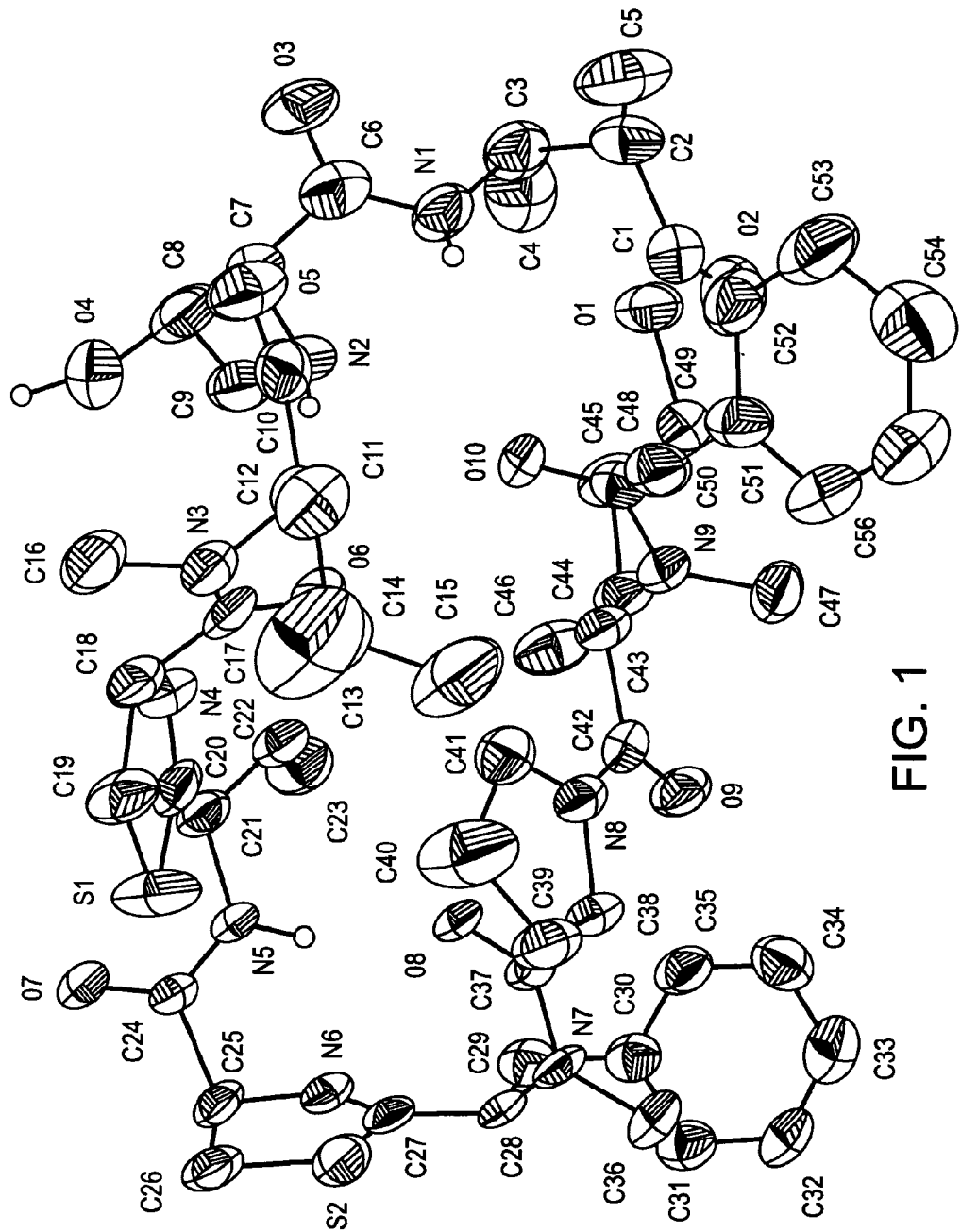
FIG. 1. depicts displacement ellipsoids (50% probability) for the X-ray crystal structure of grassypeptolide (1).
Figure 2:
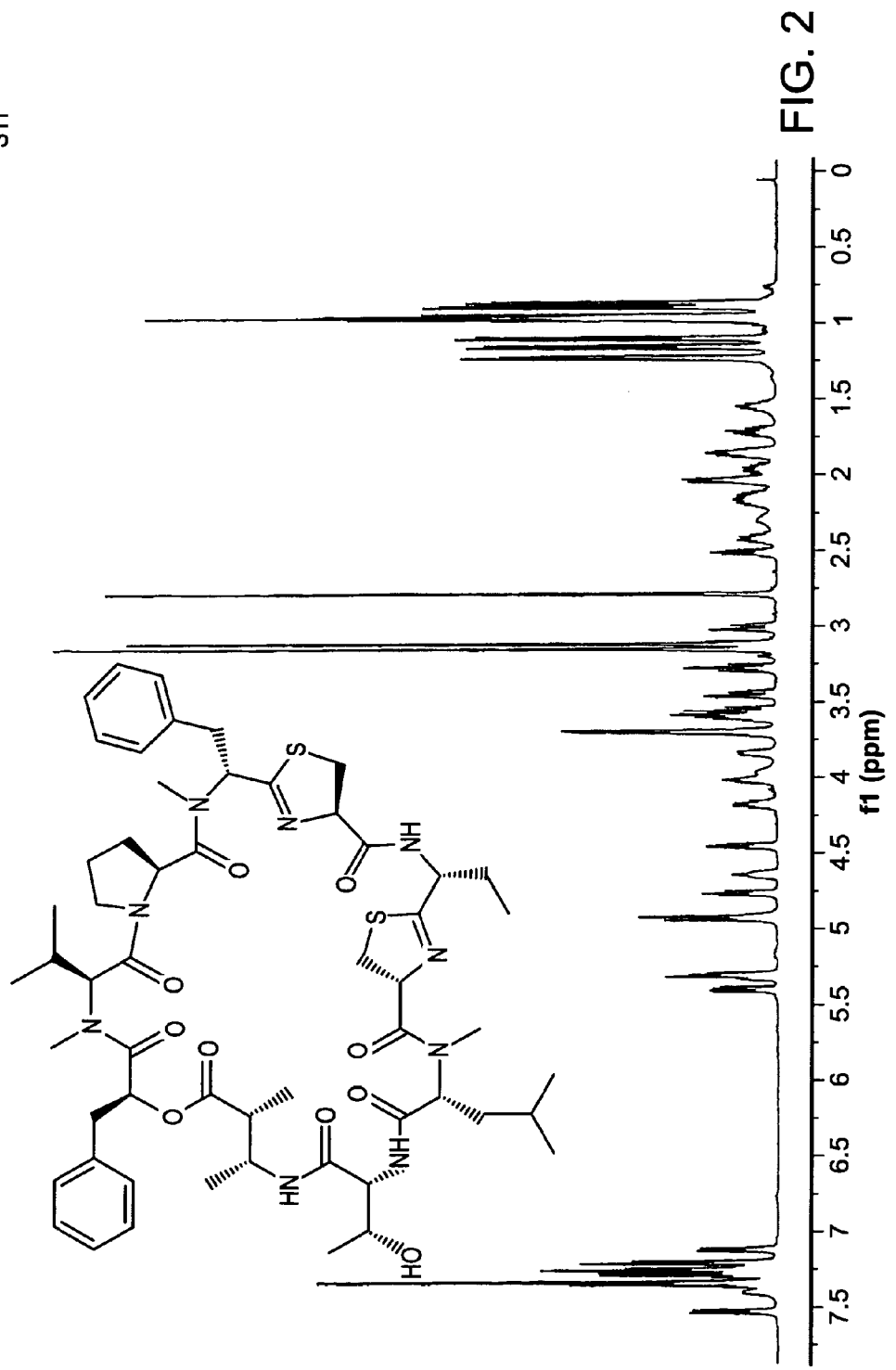
FIG. 2. depicts the $^1$H NMR spectrum of grassypeptolide (1) in CDCl$_3$ FIG. 3. depicts the $^{13}$C NMR spectrum of grassypeptolide (1) in CDCl$_3$ FIG. 4. depicts the COSY spectrum of grassypeptolide (1) in CDCl$_3$ FIG. 5. depicts the HMQC spectrum of grassypeptolide (1) in CDCl$_3$ FIG. 6. depicts the HMBC spectrum of grassypeptolide (1) in CDCl$_3$ FIG. 7. depicts the ROESY spectrum of grassypeptolide (1) in CDCl$_3$ FIG. 8. depicts the $^1$H NMR spectrum of grassypeptolide (1) in DMSO-d$_6$ FIG. 9. depicts the $^{13}$C NMR spectrum of grassypeptolide (1) in DMSO-d$_6$ FIG. 10. depicts the COSY spectrum of grassypeptolide (1) in DMSO-d$_6$ FIG. 11. depicts the TOCSY spectrum of grassypeptolide (1) in DMSO-d$_6$ FIG. 12. depicts the HSQC spectrum of grassypeptolide (1) in DMSO-d$_6$ FIG. 13. depicts the HMBC spectrum of grassypeptolide (1) in DMSO-d$_6$ FIG. 14. depicts the ROESY spectrum of grassypeptolide (1) in DMSO-d$_6$
Figure 3:
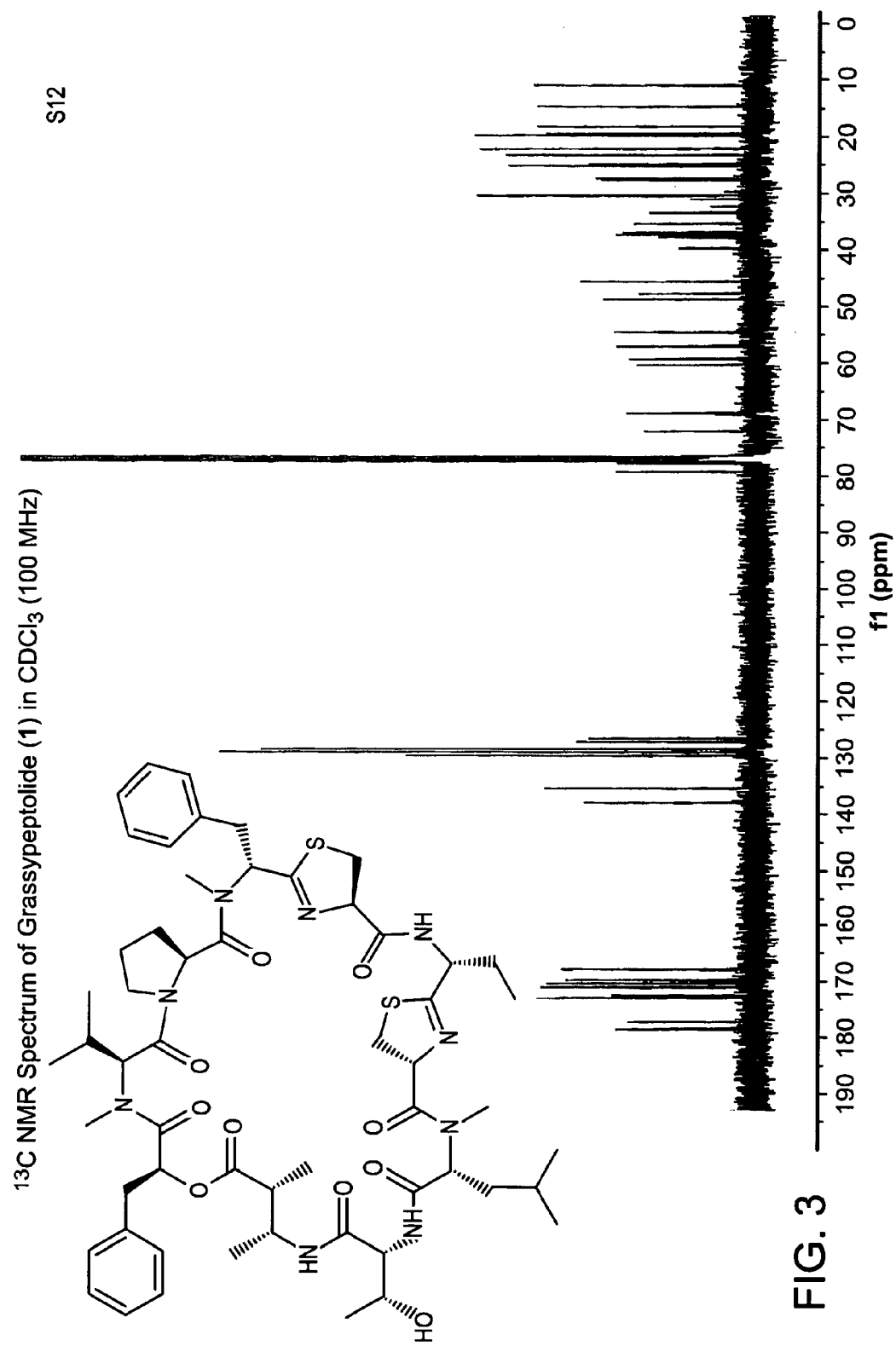
Figure 4:
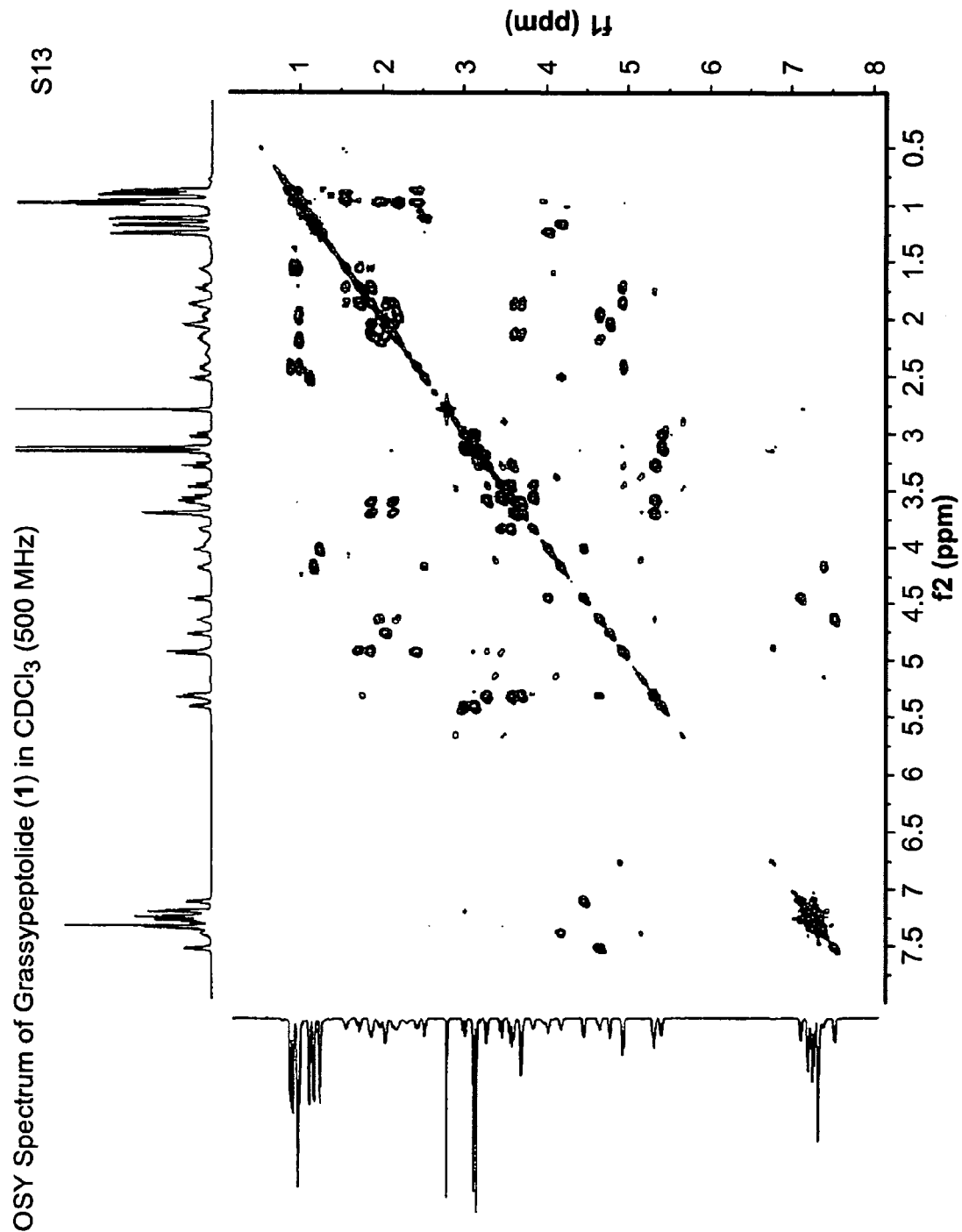
Figure 5:
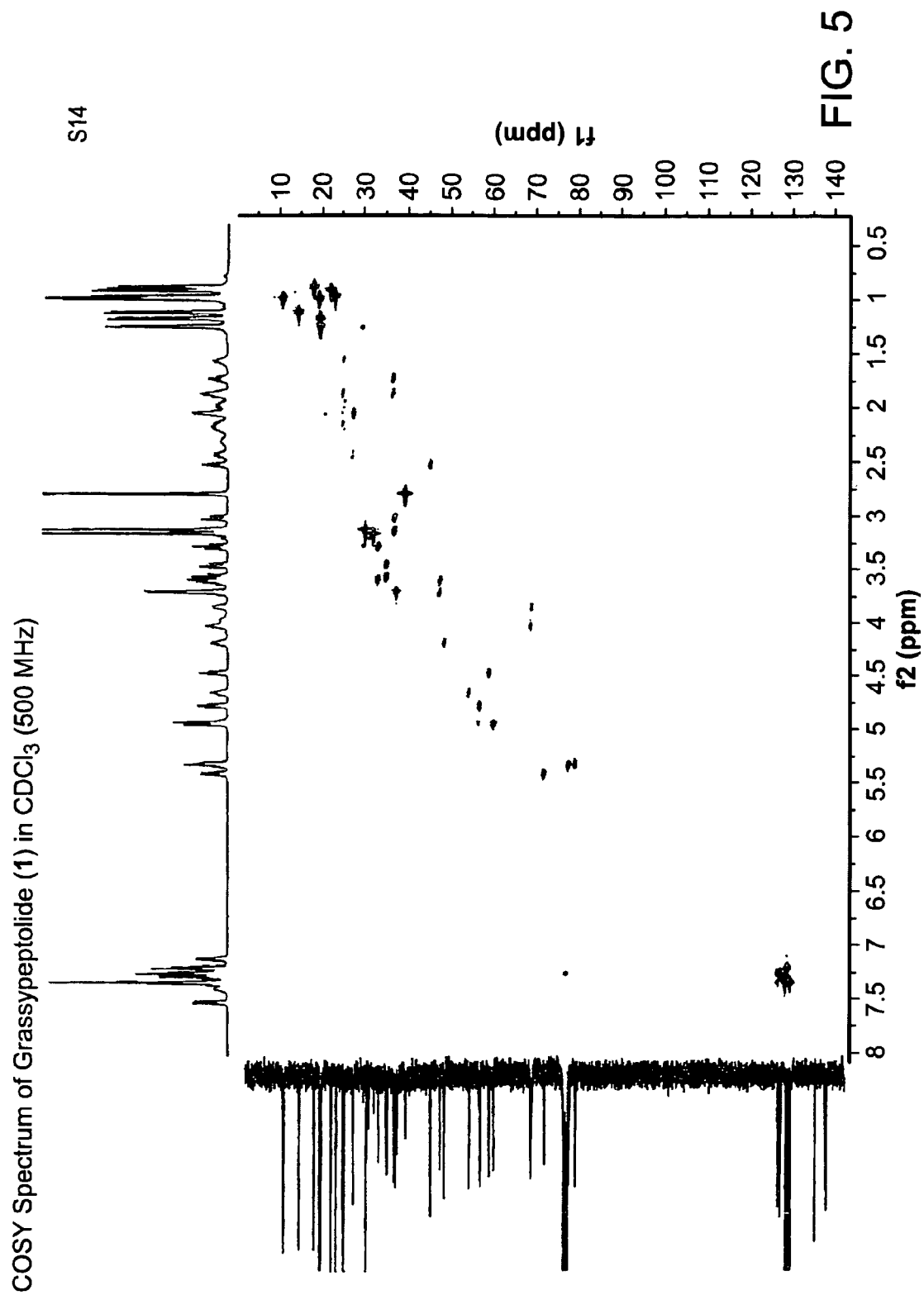
Figure 6:
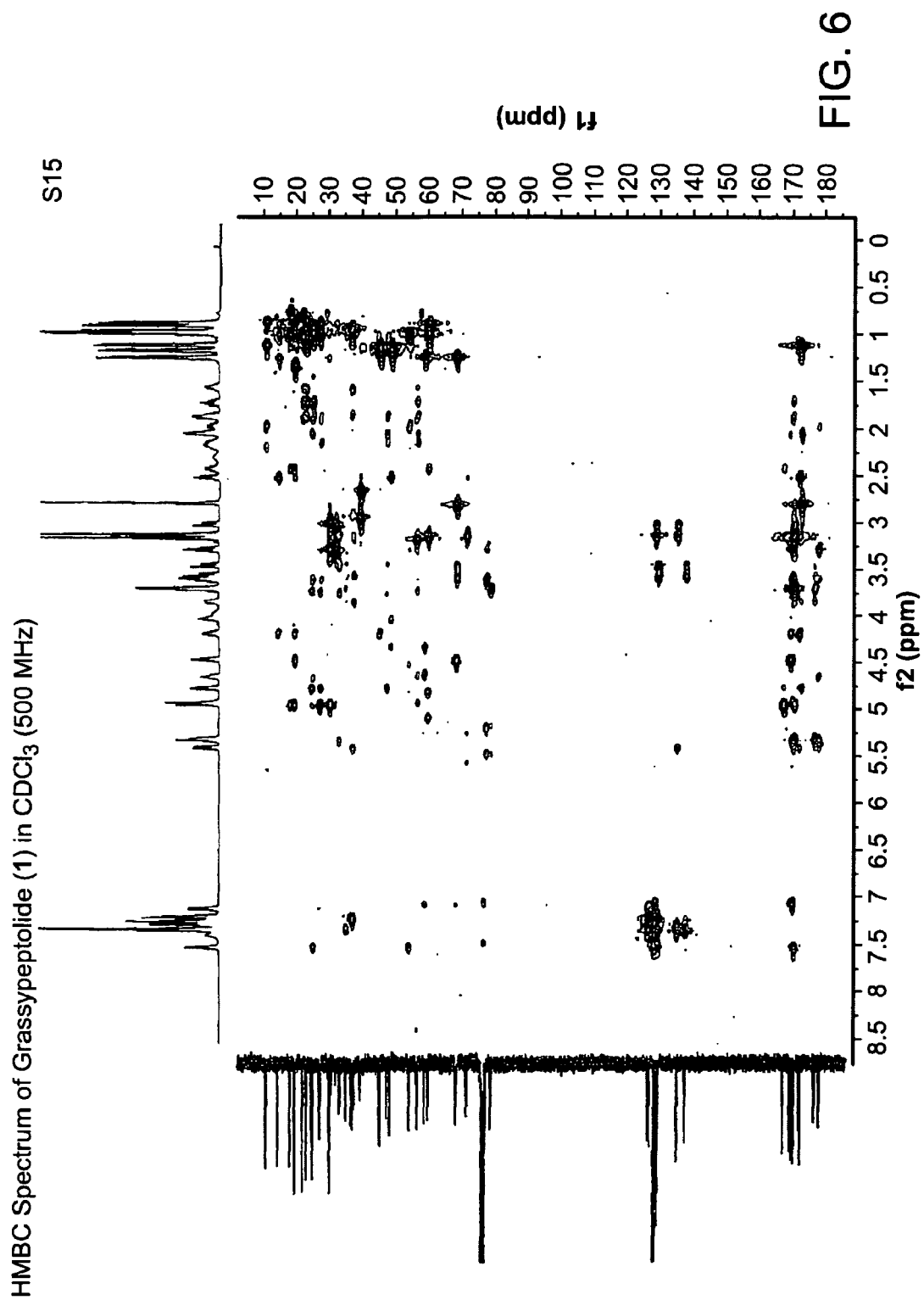
Figure 7:
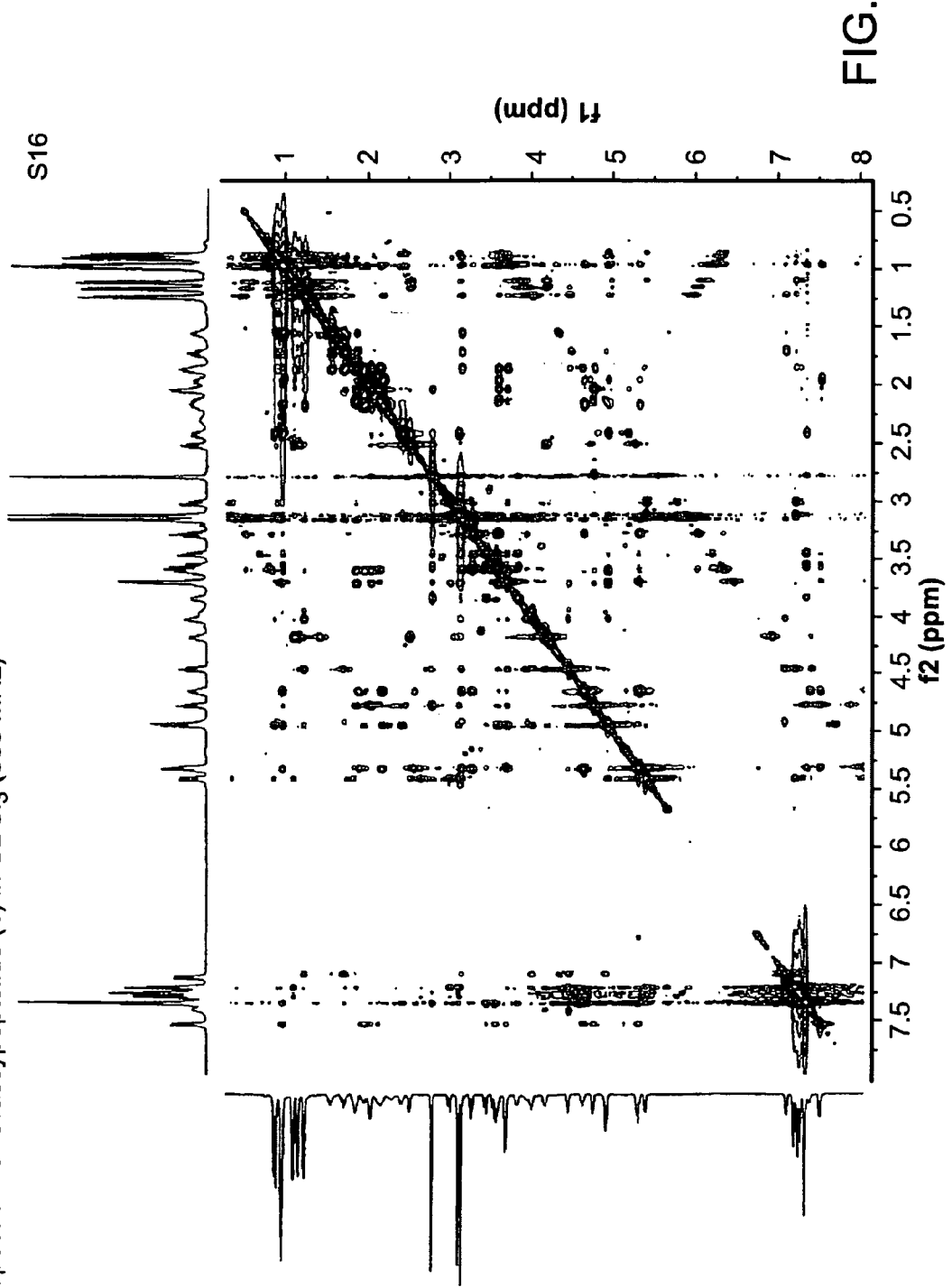
Figure 8:
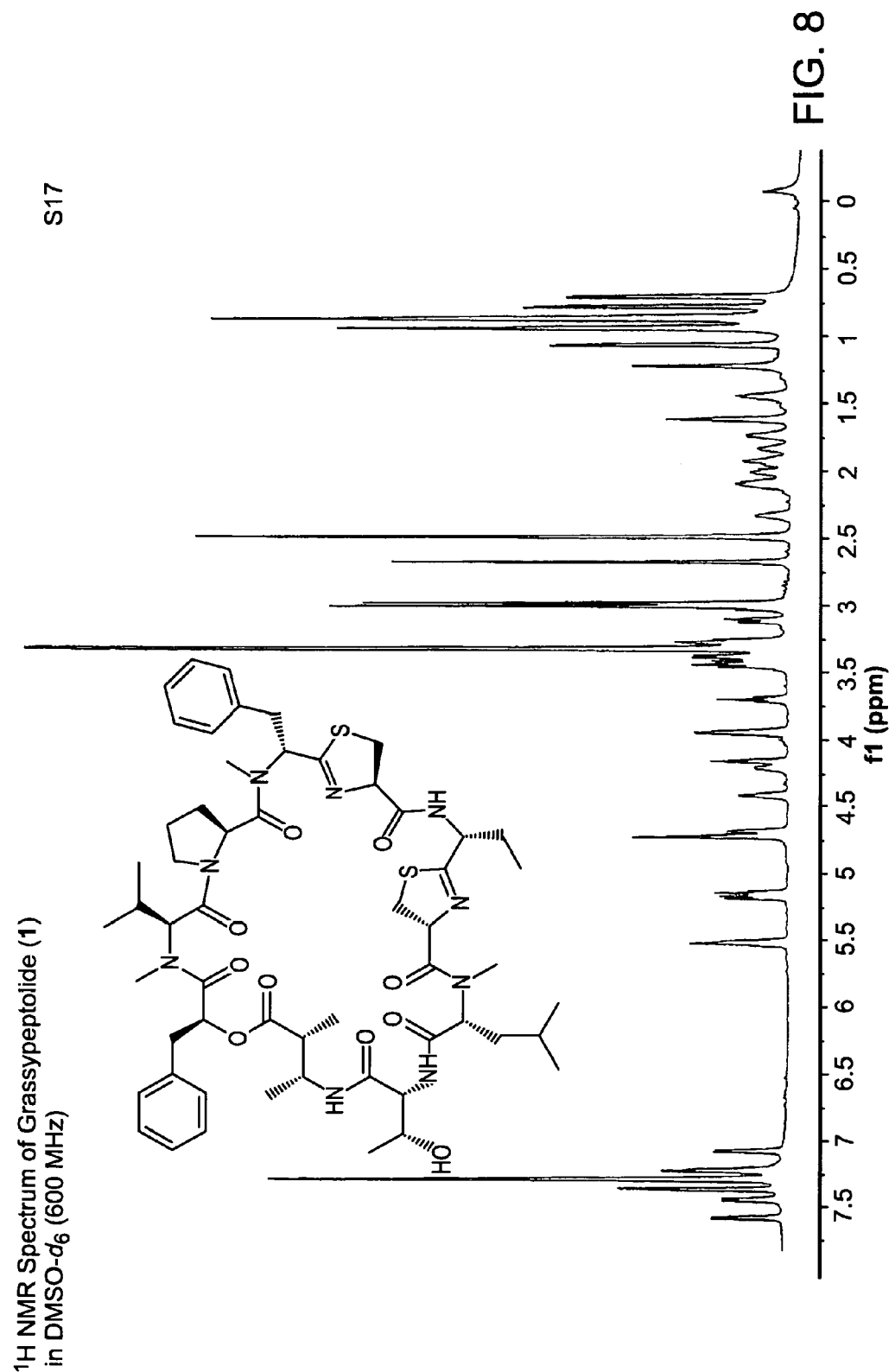
Figure 9:
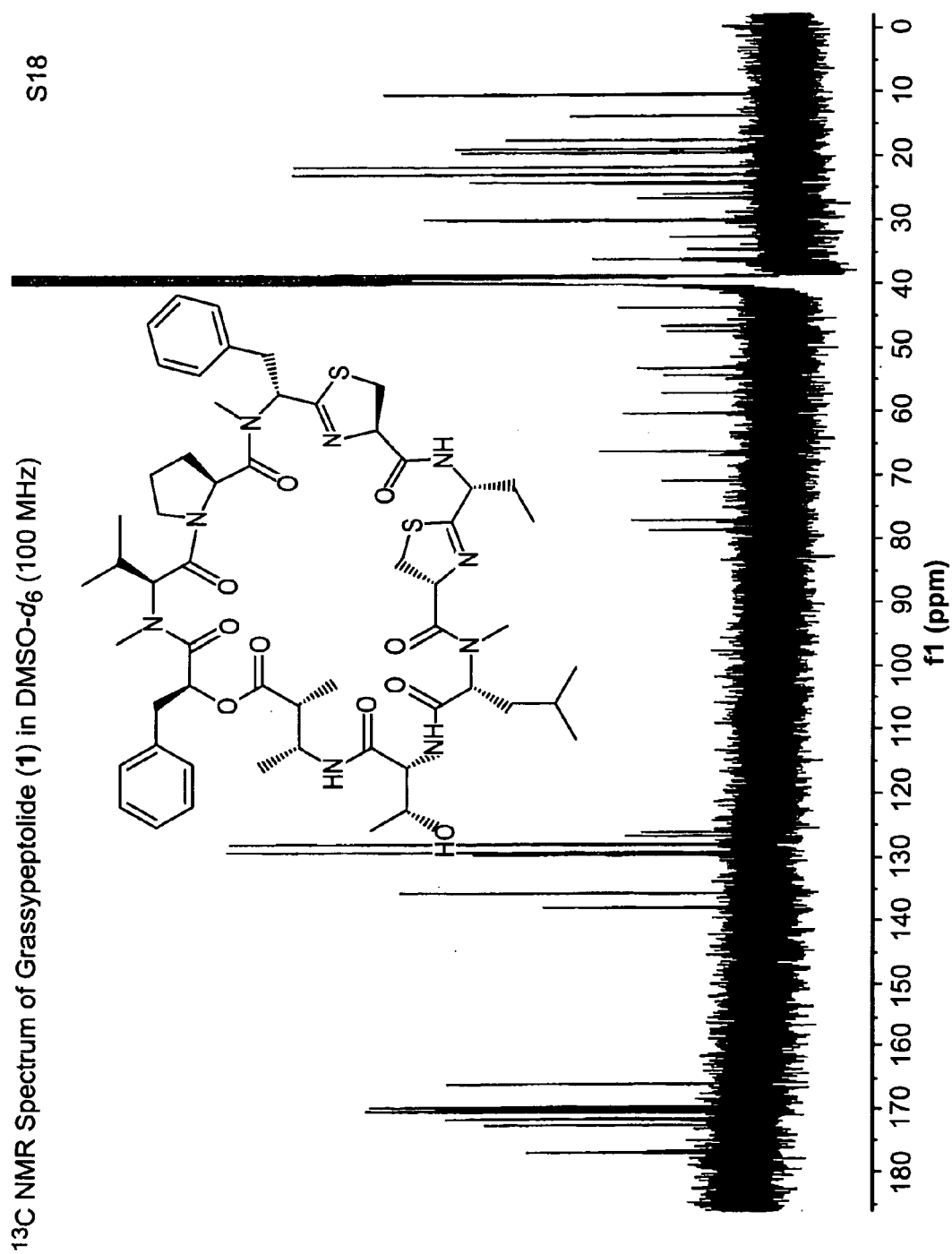
Figure 10:
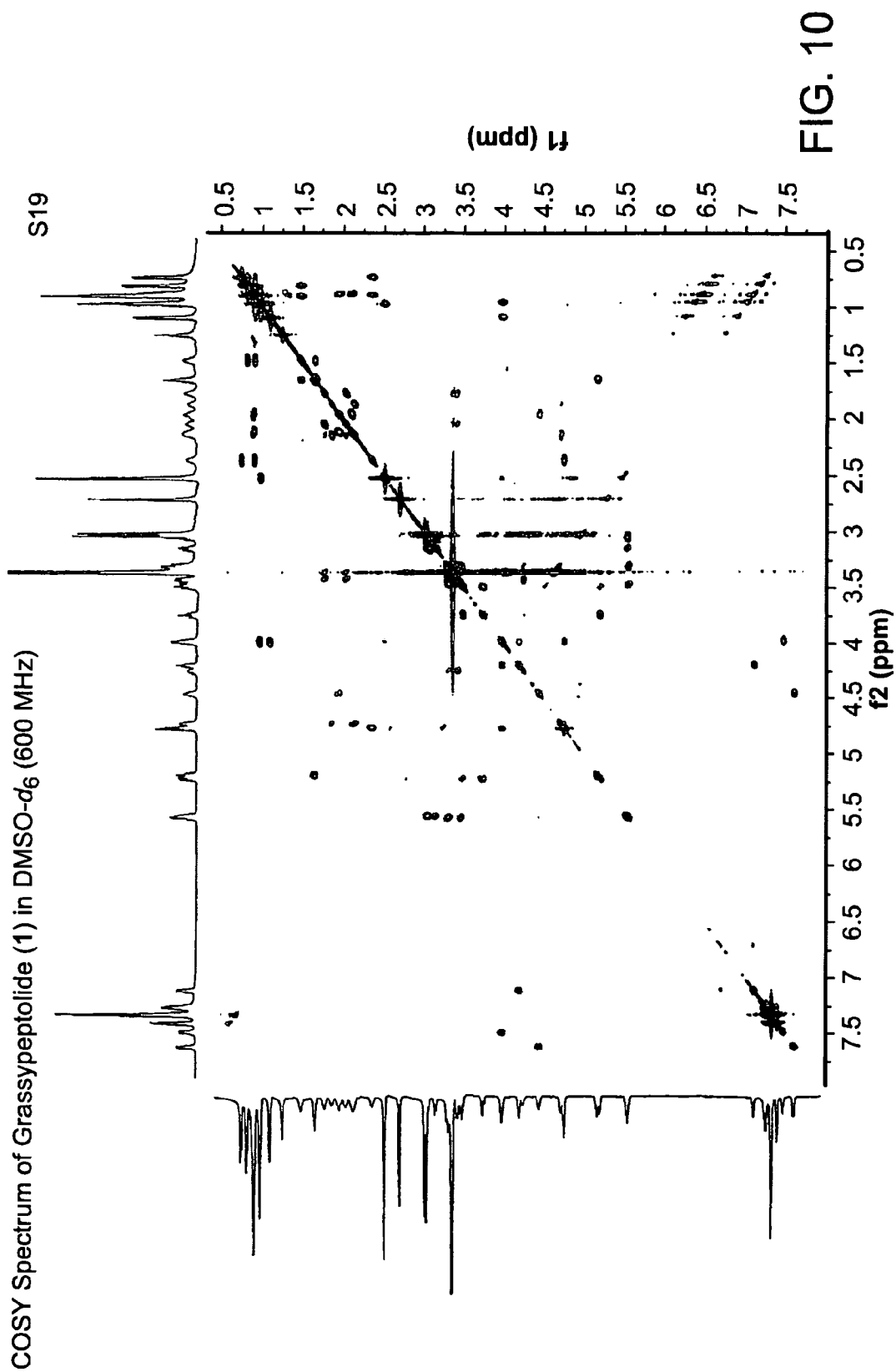
Figure 11:
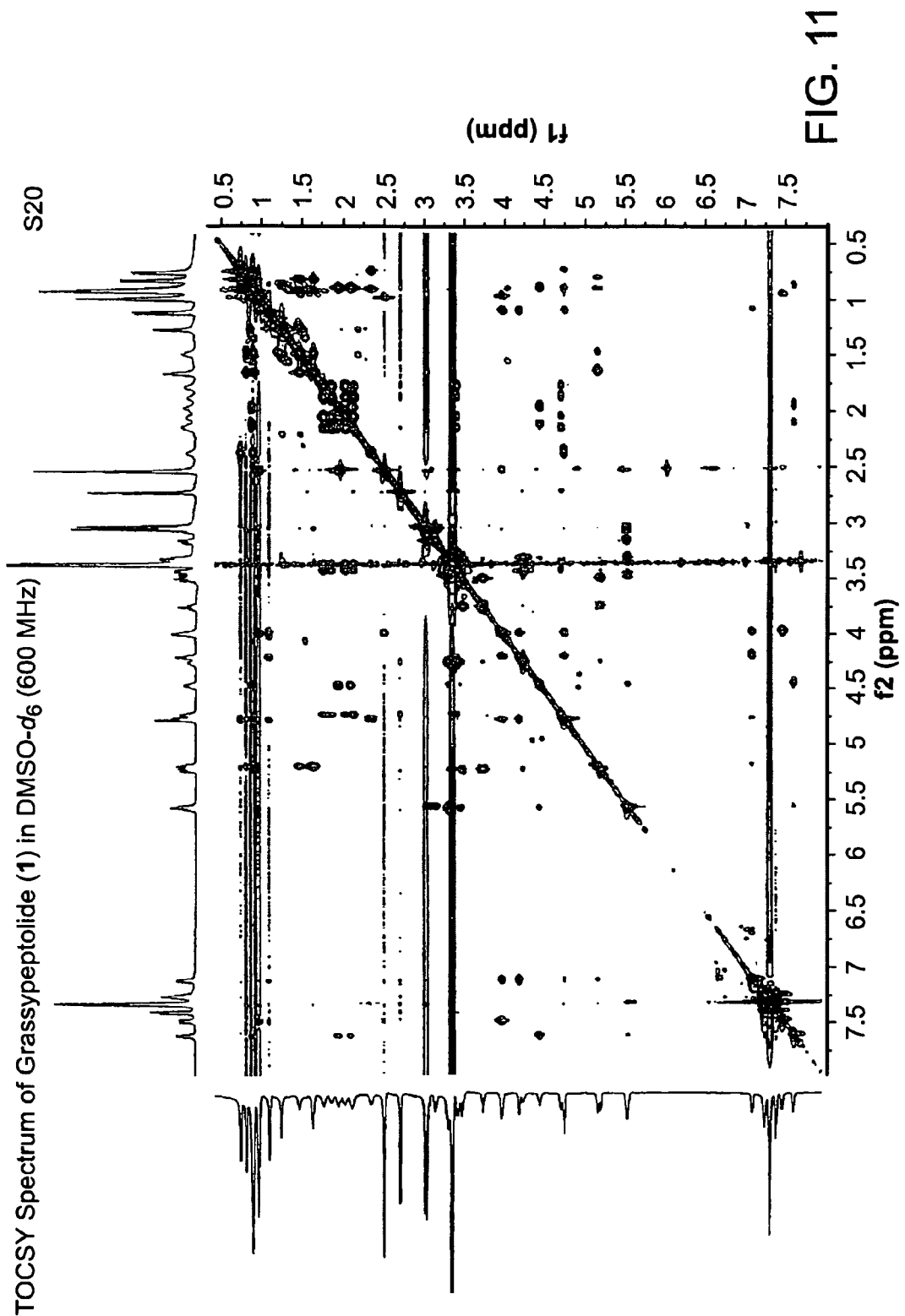
Figure 12:
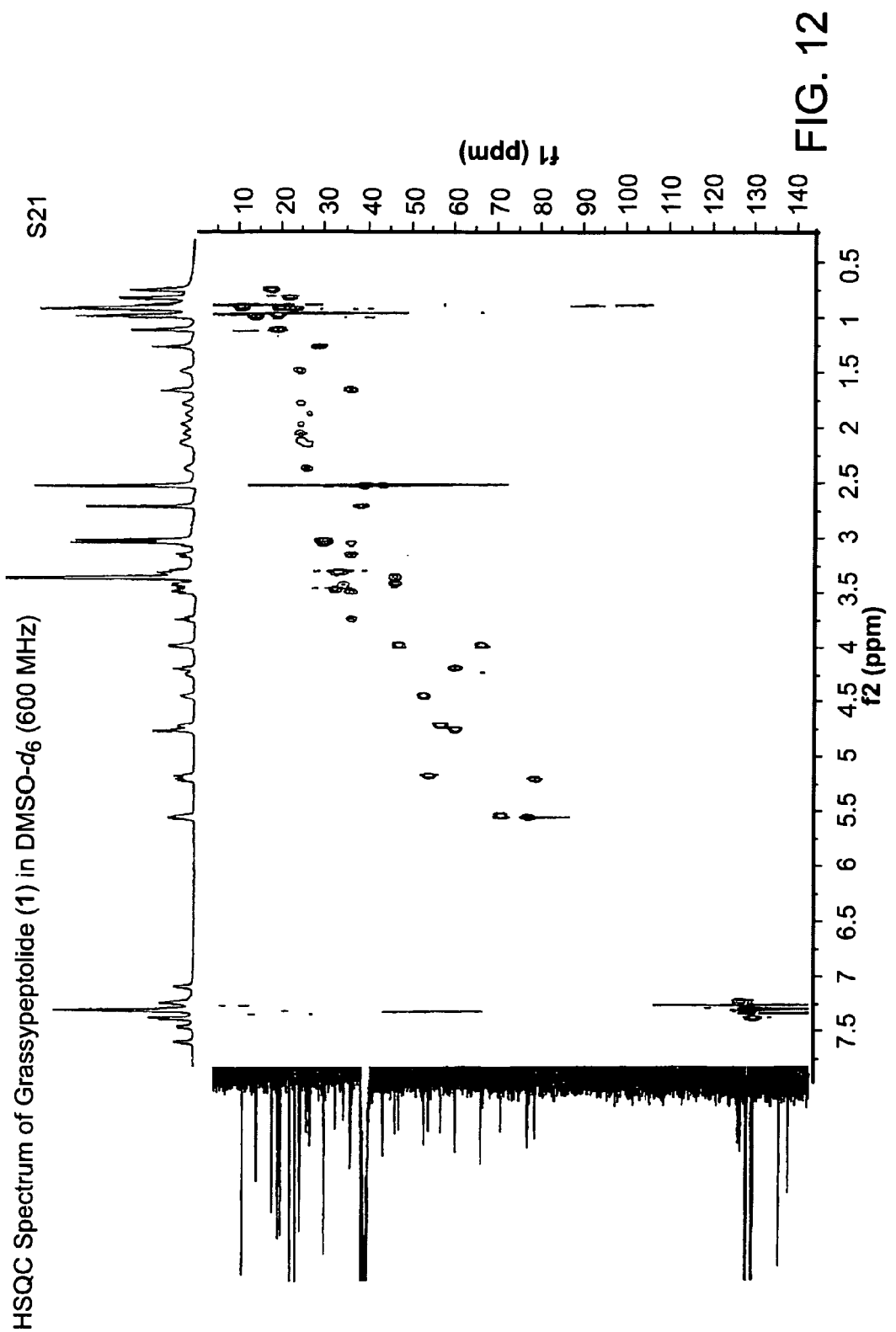
Figure 13:
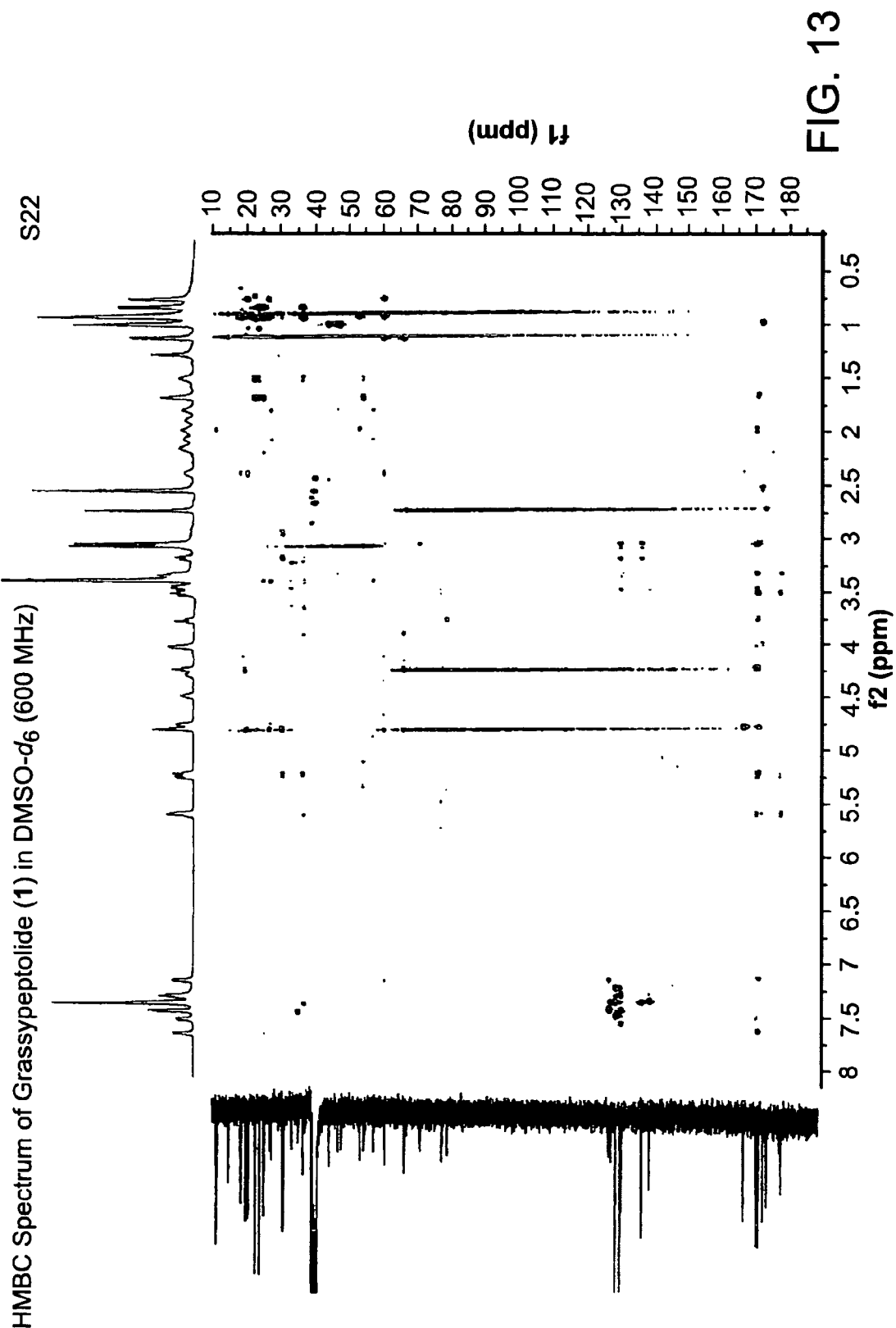
Figure 14:
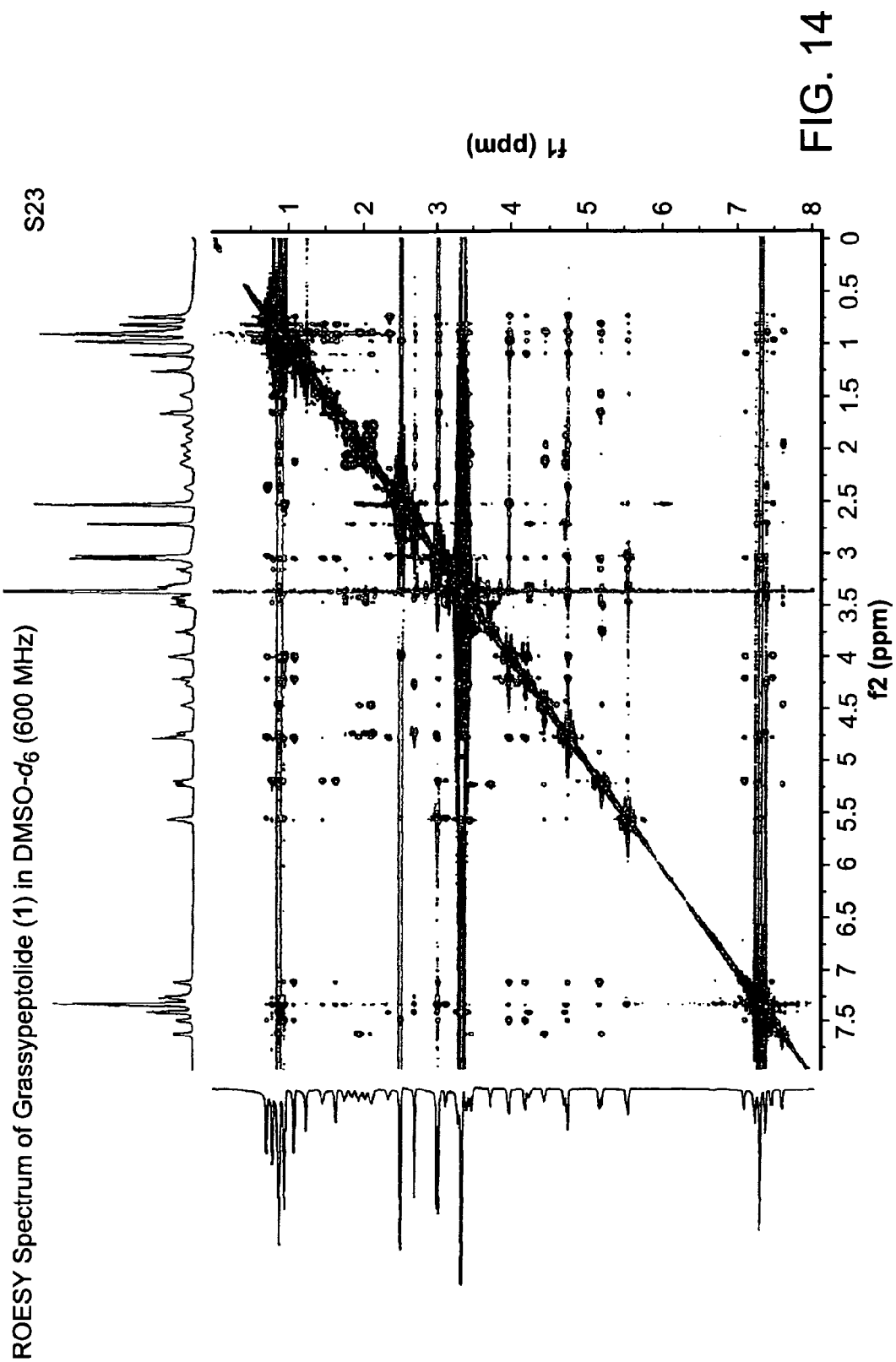

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. Suitable substituents include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)R$^{17}$, NR$^{15}$C(O)R$^{17}$, S(O)R$^{17}$, S(O)$_2$R$^{17}$, R$^{16}$, oxo, C(O)R$^{16}$, C(O)(CH$_2$)nOH, (CH$_2$)nOR$^{15}$, (CH$_2$)nC(O)NR$^{15}$R$^{16}$, NR$^{15}$S(O)$_2$R$^{17}$, where n is independently 0-6 inclusive. Each R$^{15}$ is independently hydrogen, C$_1$-C$_4$ alkyl or C$_3$-C$_6$ cycloalkyl. Each R$^{16}$ is independently hydrogen, alkenyl, alkynyl, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, NH$_2$, C$_1$-C$_4$ alkylamino, C$_1$-C$_4$ dialkylamino, C$_1$-C$_2$ perfluoroalkyl, C$_1$-C$_2$ perfluoroalkoxy, or 1,2-methylenedioxy.

Compounds of the Invention and Structure Elucidation

Samples of *L. confervoides* were collected off Grassy Key.[6] The non-polar extract (EtOAc/MeOH 1:1) was fractionated over HP-20 resin followed by silica chromatography and reversed-phase HPLC to afford 1 {[α]$^{20}_D$ +76 (c 0.1, CH$_2$Cl$_2$)}. NMR data combined with a [M+H]$^+$ peak at m/z 1102.5438 in the HRESIMS of 1 suggested a molecular formula of C$_{56}$H$_{79}$N$_9$O$_{10}$S$_2$ (calcd for C$_{56}$H$_{80}$N$_9$O$_{10}$S$_2$, 1102.5464). The $^1$H NMR spectrum of 1 in CDCl$_3$ was indicative of a peptide by displaying three secondary amide doublets ($\delta_H$ 7.12, 7.40, 7.53), three putative N-Me tertiary amide singlets ($\delta_H$ 2.78, 3.11, 3.15) and several resonances characteristic for α-protons of amino acids ($\delta_H$ ~4 to ~5). Considering the IR spectrum, which exhibited bands due to ester (1733 cm$^{-1}$) and amide (1640 cm$^{-1}$) carbonyl stretch vibrations, 1 appeared to be a depsipeptide.

TABLE 1

$^1$H and $^{13}$C NMR Spectral Data for Compound 1 in CDCl$_3$ (δ in ppm, J in Hz) at 500 MHz ($^1$H) and 100 MHz ($^{13}$C)

| C/H | $\delta_H$ (J) | $\delta_C{}^a$ | HMBC$^b$ |
|---|---|---|---|
| 1 | | 172.5, s | |
| 2 | 2.51, qd (6.9, 6.2) | 45.5, d | 1, 3, 4, 5, 49$^d$ |
| 3 | 4.18, dqd (6.8, 6.7, 6.2) | 48.6, d | 1, 2, 4, 5, 6 |
| 4 | 1.16, d (6.7) | 19.7,$^c$ q | 2, 3 |

TABLE 1-continued $^1$H and $^{13}$C NMR Spectral Data for Compound 1 in CDCl$_3$ (δ in ppm, J in Hz) at 500 MHz ($^1$H) and 100 MHz ($^{13}$C)

| C/H | δ$_H$ (J) | δ$_C$$^a$ | HMBC$^b$ |
|---|---|---|---|
| 5 | 1.10, d (6.9) | 14.6, q | 1, 2, 3 |
| NH | 7.40, br d (6.8) | | |
| 6 | | 169.8, s | |
| 7 | 4.45, dd (7.8, 6.4) | 59.2, d | 6, 8, 9, 10 |
| 8 | 4.02, dq (6.4, 6.2) | 68.8, d | |
| 9 | 1.23, d (6.2) | 19.7,$^c$ q | 7, 8 |
| OH | 3.96, br | | |
| NH | 7.12, d (7.8) | | 7, 8, 10 |
| 10 | | 170.3, s | |
| 11 | 4.92, br | 56.7, d | 13, 17 |
| 12a | 1.85, m | 36.9, t | 10, 11, 13, 14, 15 |
| 12b | 1.72, ddd (−14, 8.1, 6.2) | | 10, 11, 13, 14, 15 |
| 13 | 1.55, m | 25.1, d | 11, 14, 15 |
| 14 | 0.95, d (6.6) | 23.2, q | 12, 13, 15 |
| 15 | 0.90, d (6.5) | 22.1, q | 12, 13, 14 |
| 16 | 3.15, s | 32.3, q | 11, 17 |
| 17 | | 170.4, s | |
| 18 | 5.32, ddd (9.5, 9.1, 1.8) | 77.8, d | 17, 19, 20 |
| 19a | 3.58, dd (−9.9, 9.1) | 33.4, t | 17, 18, 20 |
| 19b | 3.27, dd (−9.9, 9.5) | | 17, 18, 20 |
| 20 | | 178.5, s | |
| 21 | 4.64, m | 54.4, d | 20 |
| 22a | 2.18, m | 25.2, t | 23 |
| 22b | 1.97, m | | 20, 21, 23 |
| 23 | 0.96, t (7.2) | 11.0, q | 21, 22 |
| NH | 7.53, d (7.9) | | 21, 22, 24 |
| 24 | | 171.0, s | |
| 25 | 5.30, m | 79.3, d | 24, 27 |
| 26a/b | 3.70, m (2H) | 37.7, t | 24, 25, 27 |
| 27 | | 177.2, s | |
| 28 | 3.83, dd (9, 3.5) | 69.0, d | 27, 37 |
| 29a | 3.57, dd (−13.9, 9) | 35.3, t | 27, 28, 30, 31/35 |
| 29b | 3.44, dd (−13.9, 3.5) | | 28, 30, 31/35 |
| 30 | | 138.2, s | |
| 31/35 | 7.35, m | 129.8, d | 29, 33 |
| 32/34 | 7.34, m | 128.7, d | 30 |
| 33 | 7.25, m | 126.7, d | |
| 36 | 2.78, s | 39.6, q | 28,37 |
| 37 | | 173.0, s | |
| 38 | 4.77, dd (7.4, 5.5) | 57.0, d | 37, 39, 40, 41, 42 |
| 39a/b | 2.04, m (2H) | 27.5, t | 37, 38, 40, 41 |
| 40a | 2.12, m | 24.8, t | 38, 39, 41 |
| 40b | 1.86, m | | 38, 39, 41 |
| 41a | 3.69, m | 47.6, t | 38, 39, 40 |
| 41b | 3.60, m | | 39, 40 |
| 42 | | 167.8, s | |
| 43 | 4.93, d (10.9) | 60.3, d | 42, 44, 45, 46, 47, 48 |
| 44 | 2.42, dqq (10.9, 6.7, 6.4) | 27.3, d | 42, 43, 45, 46 |
| 45 | 0.97, d (6.4) | 19.5, q | 43, 44 |
| 46 | 0.87, d (6.7) | 18.2, q | 43, 44, 45 |
| 47 | 3.11, s | 30.3, q | 43, 48 |
| 48 | | 171.1, s | |
| 49 | 5.40, dd (9.9, 3.5) | 72.0, d | 1, 50, 51 |
| 50a | 3.12, dd (−14.5, 9.9) | 37.2, t | 49, 51, 52/56 |
| 50b | 3.00, dd (−14.5, 3.5) | | 48, 51, 52/56 |
| 51 | | 135.6, s | |
| 52/56 | 7.21, m | 129.2, d | 50, 54 |
| 53/55 | 7.30, m | 128.6, d | 51 |
| 54 | 7.26, m | 127.3, d | 52/56 |

$^6$Collection site position: 24° 43.381' N, 80° 51.696' W.
$^a$Multiplicity deduced from APT and HMQC spectra.
$^b$Protons showing long-range correlation to indicated carbon.
$^c$These carbons have the same chemical shift.
$^d$An unusual four-bond HMBC$^7$ (see text).

Analysis of the $^1$H NMR, $^{13}$C NMR, APT, COSY, HMQC, HMBC and ROESY spectra recorded in CDCl$_3$ revealed the presence of two regular α-amino acid units (threonine, C6-9; proline; C37-41), two N-methylated α-amino acids (N-methylleucine, C10-16; N-methylvaline, C42-47), one β-amino acid (Maba, C1-5), phenylacetic acid (Pla, C48-56), a N-methylphenylalanine-derived thiazoline carboxylic acid unit (N-Me-Phe-thn-ca; C24-36), and a thiazoline carboxylic acid moiety derived from Aba (Aba-thn-ca; C17-23) (Table 1). The presence of the two thiazoline rings was deduced from the chemical shifts of vicinally coupled H-18 (δ$_H$ 5.32) and H$_2$-19ab (δ$_H$ 3.58/3.27) as well as H-25 (δ$_H$ 5.30) and H$_2$-26ab (δ$_H$ 3.70) combined with HMBC correlations of these spin systems to putative carbonyl-derived carbons from Aba [C-20 (δ$_C$ 178.5)] and N-Me-Phe [C-27 (δ$_C$ 177.2), respectively. In addition, 1D selective TOCSY experiments revealed homoallylic coupling in both thiazoline rings between H-18/H-21 and H-25/H-28. HMBC analysis (Table 1) readily established the connectivity of the units as shown for 1, which was further confirmed by interresidue ROESY correlations. Notably, there was an unusual four-bond correlation between H-2 and C49, which could have arisen because of a planar "W" conformation.$^7$ $^7$Claridge, T. D. W. High-Resolution NMR Techniques in Organic Chemistry; Elsevier: San Diego, Calif., 1999.

Compound 1 was hydrolyzed with 6 N HCl (110° C., 18 h) and the hydrolyzate subjected to chiral HPLC, revealing the presence of D-Aba, N-Me-D-Phe, L-Pro, N-Me-L-Val, L-Pla, and D-allo-Thr in the molecule, but the correct assignment for N-Me-Leu remained unclear. A sample of 1 was also subjected to ozonolysis prior to hydrolysis in an attempt to detect cysteic acid (Cya), and hence deduce the configuration of the thiazoline rings. However, peaks for both L- and D-Cya were detected by chiral HPLC, preventing unambiguous configurational assignment. Marfey's analysis$^8$ of the hydrolyzed ozonolysis product was carried out to ascertain the configuration of the Maba,$^{9,10}$ N-Me-Leu and Cya units, using 1-fluoro-2,4-dinitrophenyl-5-L-leucinamide (L-FDLA) as the derivatizing agent. Reversed-phase HPLC of 1 derivatized with L-FDLA allowed the assignment of (2R,3R)-Maba.$^{11}$ In addition, the presence of D-allo-Thr, N-Me-D-Phe,$^{12}$ L-Pro and N-Me-L-Val were confirmed, and N-Me-Leu could be unambiguously assigned. L-FDLA adducts for L- or D-Cya were quantified by LC-MS and found present in the ratio of 1.64:1, indicating that either the thiazolines were of opposite configuration producing cysteic acids in different yields, or that epimerization of one or both units had occurred. However, presumably at least one thiazoline had to have R configuration because of the excess L-Cya produced.

$^8$Marfey, P. Carlsberg Res. Commun. 1984, 49, 591-596.
$^9$Only the 2R,3R and 2R,3S standards were used. The elution times of the 2S,3S and 2S,3R isomers were deduced by derivatizing these standards with DL-FDLA.
$^{10}$(a) Fujii, K.; Ikai, Y.; Mayumi, T.; Oka, H.; Suzuki, M.; Harada, K.-I. Anal. Chem. 1997, 69, 3346-3352. (b) Fujii, K.; Ikai, Y.; Oka, H.; Suzuki, M.; Harada, K.-I. Anal. Chem. 1997, 69, 5146-5151.
$^{11}$Two peaks were observed corresponding to (2R,3R)- and (2S,3R)-Maba in the approximate ratio of 2.5:1. This is consistent with chromatograms of the standards, which were obtained from the corresponding N-benzoylated-O-methyl esters. The latter also showed some epimerization at the 2-position during hydrolysis.
$^{12}$Marfey's adducts of N-Me-D-Phe and N-Me-L-Leu co-eluted; however, the relative intensity of the corresponding peak was reduced and N-Me-D-Glu was generated when stringent ozonolysis conditions (25° C.) were employed. Thus, a N-Me-D-Phe residue was present in 1.

Attempts were then made to crystallize the compound. Eventually a small yield of crystals was produced using a mixture of dichloromethane and methanol.$^{13}$ The resulting X-ray structure (FIG. 1) confirmed the gross 2D arrangement and all the previously assigned stereocenters. Additionally, both thiazolines could be assigned as R, confirming that significant epimerization had occurred under the reaction conditions.

$^{13}$One methanol molecule was seen incorporated into the lattice. Upon drying, the crystals would quickly degrade, presumably due to methanol loss.

The crystal structure shows hydrogen bonds between the NH (at N1) of Maba to the Thr N (N2; 2.35 Å) and the Pla ester O (O1; 2.52 Å). Another hydrogen bond occurs between the Thr NH and the carbonyl of Aba-thn-ca (O6; 2.37 Å). At the opposite site of the macrocycle, a tight turn at N-Me-Phe-thn-ca is stabilized by a hydrogen bond (2.04 Å) between the Pro carbonyl (O8) and the NH of Aba-thn-ca (at N5), with the angle between the planes of the thiazoline rings at almost 90°. Analogous turns occur in patellamide D at the oxazoline rings, while the thiazoles are planar.[14] In Lissoclinamide 7, a turn is centered around the other thiazoline (ring X), and there is a hydrogen bond between the NH of Phe and the N of the adjacent thiazoline, rather than across the turn. The angle between thiazoline planes is still close to 90°, but one is twisted so that its plane is parallel to that of the macrocycle.

[14]Schmitz, F. J.; Ksebati, M. B.; Chang, J. S.; Wang, J. L.; Hossain, M. B.; van der Helm, D.; Engel, M. H.; Serban, A.; Silfer, J. A. *J. Org. Chem.* 1989, 54, 3463-3472.

Several aspects of the NMR data for 1 suggested that the solution structure was similar to the X-ray structure.[15] Firstly, ROESY data suggested that all amide bonds were trans in solution, as they are in the solid state. Secondly, three calculated Φ angles from $^3J_{NH-\alpha H}$ values[16] were similar to those observed in the X-ray structure. Thirdly, the planar "W" suggested by the four-bond HMBC between H-2 and C49 was present in the X-ray structure.

[15]For conformational analysis in solution, NMR data for 1 in DMSO-$d_6$ was used, as the differing overlap of peaks allowed the unambiguous assignment of more correlations across units. The four-bond HMBC referred to was only observed in CDCl$_3$.

[16]Using modified Karplus equation $^3J_{NH-\alpha H}$=8.40 cos$^2$Φ-1.36 cos Φ+0.33, see Võgeli, B.; Ying, J.; Grishaev, A.; Bax, A. *J. Am. Chem. Soc.* 2007, 129, 9377-9385.

To investigate the solution structure, 46 distance constraints were derived from ROESY spectra[15] and three dihedral angle constraints from coupling constants (NH-αH). Using a previously established molecular modeling protocol suitable for cyclodepsipeptides,[17] ten randomly drawn structures of 1 were subjected to distance geometry,[18] followed by simulated annealing and finally restrained molecular dynamics simulation for 1 ns. The modeled structures could be divided into two distinct conformational families. Six structures bore striking similarity to the X-ray structure. The other four structures had altered macrocyclic ring conformation due to a differing orientation of the Pla-Maba-Thr region, but consistently violated the same constraint between one Maba methyl (H$_3$-5) and H-11 (N-Me-Leu). Additionally, this second conformational family exhibited more constraint violations in general and had higher energies.[19] Thus, structures in the conformational family similar to the X-ray structure are in better agreement with the ROESY data, although there were not enough constraints in the Pla-Maba-Thr region (due to signal overlap) to ensure convergence of all ten random structures to the same conformation.

[17]Luesch, H.; Yoshida, W. Y.; Moore, R. E.; Paul, V. J.; Corbett, T. H. *J. Am. Chem. Soc.* 2001, 123, 5418-5423.

[18]Kuntz, I. D.; Thomason, J. F.; Oshiro, C. M. *Methods Enzymol.* 1989, 177, 159-204 and references therein.

[19] In the X-ray structure-like family, the average number of distance constraints over 1 Å was 1.3, and the average energy was 17.507 kcal/mol. The other family had an average number of 7 distance constraint violations over 1 Å and the average energy of the structures was 30.052 kcal/mol.

The antiproliferative activity of 1 was evaluated in four cell lines derived from human osteosarcoma (U2OS), cervical carcinoma (HeLa), colorectal adenocarcinoma (HT29), and neuroblastoma (IMR-32). Compound 1 showed moderate broad-spectrum activity with IC$_{50}$ values of 2.2 μM, 1.0 μM, 1.5 μM, and 4.2 μM, respectively. This data is within the range of IC$_{50}$/GI$_{50}$ values reported for Lissoclinamide 7 (53.7 nM to 21.5 μM), but in different cell lines which were not tested here.[4,20] Previously, it has been shown that the thiazolines of Lissoclinamide 7 are important to its cytotoxic activity.[4] It is tempting to speculate that this motif might also be responsible for the activity of 1, and that it might indicate a shared mechanism of action with the lissoclinamides and patellamides.

[20]Hawkins, C. J.; Lavin, M. F.; Marshall, K. A.; van den Brenk, A. L; Watters, D. J. *J. Med. Chem.* 1990, 33, 1634-1638.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an interne search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of modulating the proliferation activity of a cell in a subject, comprising contacting the subject with a compound of formula I, in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of formula I.

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of formula I, such that said subject is treated for said disorder.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In certain embodiments, the invention provides a method as described above, wherein the compound of formula I is grassypeptolide.

In certain embodiments, the invention provides a method of treating a disorder, wherein the disorder is cancer (e.g., breast, colon) or solid tumor.

In certain embodiments, the subject is a mammal, preferably a primate or human.

In another embodiment, the invention provides a method as described above, wherein the effective amount of the compound of formula I ranges from about 0.005 µg/kg to about 200 mg/kg. In certain embodiments, the effective amount of the compound of formula I ranges from about 0.1 mg/kg to about 200 mg/kg. In a further embodiment, the effective amount of compound of formula I ranges from about 10 mg/kg to 100 mg/kg.

In other embodiments, the invention provides a method as described above wherein the effective amount of the compound of formula I ranges from about 1.0 pM to about 50 µM. In certain embodiments, the effective amount ranges from about 10.0 pM to about 5 µM. In another embodiment, the effective amount ranges from about 1.0 nM to about 10 nM.

In another embodiment, the invention provides a method as described above, wherein the compound of formula I is administered intravenously, intramuscularly, subcutaneously, intracerebroventricularly, orally or topically.

In other embodiments, the invention provides a method as described above, wherein the compound of formula I is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimeterxate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease. Another object of the present invention is the use of a compound as described herein (e.g., of any formulae herein) for use in the treatment of a cell proliferation disorder or disease.

Pharmaceutical Compositions

In one aspect, the invention provides a pharmaceutical composition comprising the compound of formula I and a pharmaceutically acceptable carrier.

In one embodiment, the invention provides a pharmaceutical composition wherein the compound of formula I is grassypeptolide, and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of formula I, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The present invention will now be demonstrated using specific examples that are not to be construed as limiting.

General Experimental Procedures. Optical rotation was measured on a Perkin-Elmer 341 polarimeter. UV was measured on a SpectraMax M5 (Molecular Devices) and IR data obtained on a Bruker Vector 22 instrument. $^1$H and 2D NMR spectra in CDCl$_3$ were recorded on a Bruker Avance 500 MHz spectrometer. $^1$H and 2D NMR spectra in DMSO-d$_6$ and 1D TOCSY experiments in both CDCl$_3$ and DMSO-d$_6$ were carried out on a Bruker Avance II 600 MHz spectrometer using a 1-mm triple-resonance high-temperature superconducting cryogenic probe. All 100-MHz $^{13}$C NMR data were recorded on a Varian Mercury 400 MHz spectrometer. Spectra were referenced to residual solvent signals [$\delta_{H/C}$ 7.26/77.0 (CDCl$_3$) and $\delta_{H/C}$ 2.49/39.5 (DMSO-d$_6$)]. HMQC and HSQC experiments were optimized for 145 Hz, and HMBC experiments were optimized for 10 Hz (CDCl$_3$) and 7 Hz (DMSO-d$_6$). HRESIMS were recorded on a Bruker APEX II FTICR spectrometer in the positive mode. LC-MS data were obtained using an Agilent 1100 equipped with a ThermoFinnigan LCQ by ESI (negative mode).

Example 1

Extraction and Isolation

Extraction and Isolation. Samples of *Lyngbya confervoides* were collected off Grassy Key in the middle Florida Keys (24°43.381'N, 80°51.696'W) on May 26, 2004. A voucher specimen is maintained at the Smithsonian Marine Station. The freeze-dried organism was extracted with EtOAc-MeOH (1:1) to afford the non-polar extract (11.34 g) which was applied to a diaion HP-20 polymeric resin and subsequently fractionated with H$_2$O and increasing concentrations of acetone. The fraction eluting with 100% acetone (608 mg) was applied to a silica gel column, then eluted with increasing concentrations of isopropanol in CH$_2$Cl$_2$. The fraction eluting with 100% isopropanol was purified by semipreparative reversed-phase HPLC (YMC-Pack ODS-AQ, 250×10 mm, 2.0 mL/min; UV detection at 220 and 254 nm) using a MeOH—H$_2$O linear gradient (60-100% over 30 min, then 100% MeOH for 20 min), to furnish compound 1, $t_R$ 34.2 min (11.2 mg).

Grassypeptolide (1): Colorless amorphous solid; [α]$^{20}_D$ +76 (c 0.1, CH$_2$Cl$_2$); UV (CH$_2$Cl$_2$) λ$_{max}$ (log ∈) 230 (2.20), 260 (1.95), 330 (1.37); IR (film) ν$_{max}$ 3307 (br), 3054 (w), 2958, 2925, 2873, 2851, 1733, 1640 (s), 1532, 1456, 1266, 1085, 1023, 738, 702 cm$^{-1}$; $^1$H NMR, $^{13}$C NMR, COSY, HMBC and ROESY data see Table 1 (CDCl$_3$), Table S1 (CDCl$_3$) and Table S2 (DMSO-d$_6$); HRESIMS m/z [M+Na]$^+$ 1124.5264 (calcd for C$_{56}$H$_{79}$N$_9$O$_{10}$S$_2$Na, 1124.5284), [M+H]$^+$ 1102.5438 (calcd for C$_{56}$H$_{80}$N$_9$O$_{10}$S$_2$, 1102.5464), [M+H$_2$]$^{2+}$ 551.7756 (calcd for C$_{56}$H$_{81}$N$_9$O$_{10}$S$_2$, 551.7771).

Acid Hydrolysis and Chiral HPLC Analysis. A sample of 1 (0.2 mg) was treated with 6 N HCl at 110° C. for 18 h. The hydrolyzate was concentrated to dryness and analyzed by chiral HPLC [column, Chirex phase 3126 (D) (4.6×250 mm), Phenomenex; solvent, 2 mM CuSO$_4$; flow rate, 0.8 mL/min; detection at 254 nm] for its amino acid content. D-Allo-Thr, N-Me-L-Val, L-Pro, and D-Aba eluted at $t_R$ 21.7, 26.1, 29.2 and 34.8 min, respectively. The retention times ($t_R$, min) of the authentic amino acids were as follows: L-Thr (13.4), D-Thr (15.6), L-allo-Thr (18.7), L-Aba (21.3), D-allo-Thr (21.7), N-Me-L-Val (26.1), L-Pro (29.2), D-Aba (34.8), N-Me-D-Val (43.0), and D-Pro (64.3). To detect phenyllacetic acid (Pla), the hydrolyzate was analyzed using different chiral HPLC conditions [column, Chiralpak WH (4.6×250 mm), Daicel; solvent 2 mM CuSO$_4$; flow rate, 2.5 mL/min; detection at 254 nm]. N-Me-D-Phe eluted with the other early-eluting peaks ($t_R$ ~5.7 min), and L-Pla eluted at $t_R$ 15.6 min. There was no peak corresponding to N-Me-L-Phe. The retention times ($t_R$, min) of the authentic amino acids were as follows: N-Me-D-Phe (5.7), N-Me-L-Phe (23.5), D-Pla (11.1), and L-Pla (15.6). All other amino acid standards eluted at $t_R$<9 min.

Ozonolysis, Acid Hydrolysis and Chiral HPLC Analysis. Ozone was bubbled through a sample of 1 (0.25 mg) dissolved in 3 ml CH$_2$Cl$_2$ at room temperature for 10 min. The solution was then dried down and treated with 6 N HCl at 110° C. for 26 h. The resulting hydrolyzate was concentrated to dryness and analyzed by chiral HPLC [column, Chirex phase 3126 (D) (4.6×250 mm), Phenomenex; solvent, 2 mM CuSO$_4$-MeCN (97.5:2.5); flow rate, 0.8 mL/min; detection at 254 nm] for its amino acid content. D-Allo-Thr, N-Me-L-Val/L-Pro, L-Cya, D-Aba, and D-Cya eluted at $t_R$ 15.9, 18.4-18.8, 22.0, 23.6 and 26.9 respectively. The retention times ($t_R$, min) of the authentic amino acids were as follows: L-Thr (10.9), D-Thr (12.3), L-allo-Thr (14.9), D-allo-Thr (15.9), L-Aba (16.5), L-Pro (18.5), N-Me-L-Val (18.8), L-Cya (22.0), D-Aba (23.6), D-Cya (26.9), N-Me-D-Val (27.9), and D-Pro (38.2).

Advanced Marfey's Analysis. The N-benzoyl O-methyl esters of (2R,3R)- and (2R,3S)-2-methyl-3-aminobutyric acid (Maba) were treated with 6 N HCl at 110° C. for 22 h. The products of each reaction were dried down and made up to 50 mM solutions in water. The other amino acid standards were also made into 50 mM stock solutions in water. Then, 10 µL 1 M NaHCO$_3$ and 50 µL 1-fluoro-2,4-dinitrophenyl-5-L-leucinamide (L-FDLA, 1% w/v in acetone) were added to 25 µL of these solutions. After heating at 35° C. for 1 h, with frequent mixing, the reaction mixtures were acidified with 5 µL 2 N HCl, concentrated to dryness and then reconstituted with 250 µL MeCN—H$_2$O (1:1). FDLA derivatives of the hydrolyzate and hydrolyzed ozonolysis products were prepared in a similar way. Standards and hydrolyzates were subjected to reversed-phase HPLC analysis [column, Alltima HP C18 HL (4.6×250 mm), 5 µm, Alltech; flow rate, 1.0 mL/min; PDA detection from 200-500 nm] using a linear gradient of MeCN in 0.1% (v/v) aqueous TFA (30-70% MeCN over 50 min). L-FDLA derivatives of the synthetic Maba standards gave two peaks each in an approximate ratio of 2.5:1, indicating partial epimerization at the 2-position (this accounted for the minor peak each time). Retention times were as follows ($t_R$, min): (2R,3S)-Maba (24.3), (2S,3S)-Maba (24.6), (2R,3R)-Maba (26.4), (2S,3R)-Maba (27.0). As with the standards, there were two Maba peaks in the L-FDLA-derivatized hydrolyzate, the major corresponding with (2R,3R)- and the minor with (2S,3R)-Maba. Therefore this unit was assigned 2R,3R. All other previous assignments were confirmed by Marfey's analysis. Additionally, there was a peak corresponding to N-Me-D-Leu ($t_R$ 36.6). There were no clear peaks above the noise at the retention times expected for L- and D-Cya, so the L-FDLA-adduct mixture of the hydrolyzed ozonolysis products was subjected to LC-MS analysis [column, Zorbax Eclipse SDB-C18 (3.0× 250 mm), 5 μm, Agilent; flow rate 0.15 mL/min; UV and ESIMS detection, 338 nm and negative ion mode, respectively] using a step gradient of 0.2% HCOOH in MeCN (A) and 0.2% aqueous HCOOH (B) (5-40% A over 20 min, followed by 40-50% A over 20 min, then 50-95% A over 15 min). Both D-Cya and L-Cya were detected, eluting at $t_R$ 25.3 and 25.8 min, respectively, with peak volumes in the ratio of 1:1.64 (base peak had expected [M−H]⁻ m/z 462.1 for both). Retention times ($t_R$, min, base peak m/z) of authentic standards were as follows: D-Cya (25.3; 462.1) and L-Cya (25.8; 462.1).

X-Ray Crystallography. Data were collected at 173 K on a Siemens SMART PLATFORM equipped with a CCD area detector and a graphite monochromator utilizing $MoK_\alpha$ radiation ($\lambda$=0.71073 Å). Cell parameters were refined using up to 8192 reflections. A full sphere of data (1850 frames) was collected using the co-scan method (0.3° frame width). The first 50 frames were re-measured at the end of data collection to monitor instrument and crystal stability (maximum correction on I was <1%). Absorption corrections by integration were applied based on measured indexed crystal faces.

The structure was solved by the Direct Methods in SHELXTL6, and refined using full-matrix least squares. The non-H atoms were treated anisotropically, whereas the hydrogen atoms were calculated in ideal positions and were riding on their respective carbon atoms. All acidic protons were obtained from a Difference Fourier map and refined freely. In addition to the molecule, the asymmetric unit contains a methanol molecule. The value of the Flack x parameter is −0.16(14). A very small value and a very small standard uncertainty mean that the current enantiomer is the correct one, consistent with the analysis of chemical degradation products. We believe that the deviation of our Flack x parameter from zero is due to the low diffraction of the small crystal used thus giving weak higher 2-theta reflections. A total of 740 parameters were refined in the final cycle of refinement using 4937 reflections with I>2σ(I) to yield $R_1$ and $wR_2$ of 7.43% and 15.81%, respectively. Refinement was done using $F^2$.

Molecular Modeling. The simulations were performed on a Dell PC with a 3.2 GHz Intel Pentium 4 processor, running Sybyl 7.3 under the Ubuntu Linux 7.04 operating system. The Tripos forcefield was used for all simulations. Random starting structures were generated by drawing 1 differently in ChemDraw Ultra 10.0, then they were converted to three dimensional mol2 files using Chem3D Pro 10.0. ROESY constraints were obtained by integration of correlations in MestReNova 5.0.3-2367, of spectra obtained using the following mixing times: 100, 200, 300 and 400 ms (in DMSO-$d_6$). The correlation between the geminal protons $H_2$-22 was used as the calibration reference, as it was consistently one of the largest signals across mixing times, indicating little TOCSY-type interference. Correlations were stratified into weak, medium and strong NOEs (3.5-5.0, 2.5-3.5, <2.5 Å, respectively) for each spectrum. Interresidue correlations occurring in two or more of the spectra were used, resulting in 46 restraints. Pseudoatoms were used for methylenes where the protons could not be stereospecifically assigned, as well as for magnetically equivalent H-31/H-35. In these cases a correction of 1.0 Å per pseudoatom was added to the upper limit of the constraint. Pseudoatoms were also used in the case of methyls, although a correction was not added to constraints involving them. Additionally, torsional angle constraints could be obtained from the three amide NH signals, using a Karplus equation derived from protein φ angles.[21] For these, a relatively weak force constant of 0.005 kcal/mol deg² was used. The trans conformation of amide bonds could be ascertained by the relevant ROESY correlations. In the simulations these were locked into planar conformations using a strong force constant of 2.0 kcal/mol deg².

[21] Using modified Karplus equation $^3J_{NH-\alpha H}$=8.40 cos²Φ-1.36 cos Φ+0.33, see Vögeli, B.; Ying, J.; Grishaev, A.; Bax, J. Am. Chem. Soc. 2007, 129, 9377-9385.

The random structures were subjected to the following steps: 1. Restrained energy minimization (REM), 2. Distance geometry (DG), 3. REM, 4. Restrained molecular dynamics (RMD), and 5. REM. Chirality and distance constraints (force constant 2.0 kcal/molÅ²) were applied throughout the process. Charges were calculated in Sybyl using the Gasteiger-Huckel option, and a dielectric constant of 47.24 was used (DMSO at 20° C.). The DG procedure consisted of bounds generation, bounds smoothening, and embedding of coordinates; this was followed by an optimization procedure, where the structure was minimized then subjected to simulated annealing (SA, 2000 K to 200 K over 100,000 fs, step time 0.3 fs) and then another round of minimization. RMD was run at 500 K for 1 ns, with a step size of 1 fs. Following simulation, the structures were overlayed in PyMol 0.99rc6.

Example 3

Cell Culture

Cell culture medium was purchased from Invitrogen and fetal bovine serum (FBS) from Hyclone. Cells were propagated and maintained in DMEM medium (high glucose) supplemented with 10% FBS at 37° C. humidified air and 5% $CO_2$.

Example 4

Cell Viability Assays

HT29 colon adenocarcinoma cells were used for the bioassay-guided fractionation. To determine cell type selectivity, cells from four cancer cell lines (U2OS, HeLa, HT29 and IMR-32) were plated in 96-well format and incubated at 37° C. (5% $CO_2$) for 24 hours. A dilution series of 1 in DMSO (1 μL) was then added, and after further 48 hours of incubation the cell viability was quantified using a standard assay kit based on MTT dye according to the manufacturer's instructions (Promega).

Example 5

Grassypeptolide (1) Activity

The antiproliferative activity of 1 was evaluated in four cell lines derived from human osteosarcoma (U2OS), cervical carcinoma (HeLa), colorectal adenocarcinoma (HT29), and neuroblastoma (IMR-32). Compound 1 showed moderate broad-spectrum activity with $IC_{50}$s of 2.2 μM, 1.0 μM, 1.5 μM, and 4.2 μM, respectively. This data is within the range of $IC_{50}$ values reported for Lissoclinamide 7 (53.7 nM to 20 μM), but in different cell lines which were not tested here.[4,22]

[22] Hawkins, C. J.; Lavin, M. F.; Marshall, K. A.; van den Brenk, A. L; Watters, D. J. J. Med. Chem. 1990, 33, 1634-1638.

Incorporation by Reference

The contents of all references (including literature references, issued patents, published patent applications, and co-pending patent applications) cited throughout this application are hereby expressly incorporated herein in their entireties by reference.

Equivalents

Those skilled in the art will recognize, or be able to ascertain using no more than routine experimentation, many equivalents of the specific embodiments of the invention described herein. Such equivalents are intended with be encompassed by the following claims.

What is claimed:

1. A pharmaceutical composition comprising a compound of Formula I and a pharmaceutically acceptable carrier:

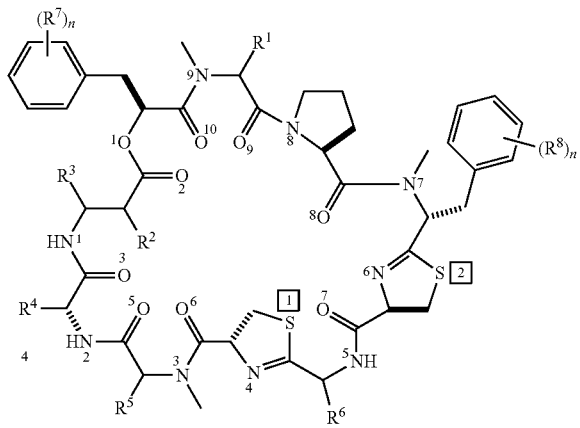

(I)

wherein:

each $R^1$ is independently H, or alkyl or aryl, each optionally substituted;

each $R^2$ is independently H, or alkyl or aryl, each optionally substituted;

each $R^3$ is independently H, or alkyl or aryl, each optionally substituted;

each $R^4$ is independently H, or alkyl or aryl, each optionally substituted;

each $R^5$ is independently H, or alkyl or aryl, each optionally substituted;

each $R^6$ is independently H, or alkyl or aryl, each optionally substituted;

each $R^7$ is independently H, or alkyl, hydroxyl, alkoxy, halo, cyano, nitro, mercapto, thioalkoxy, alkoxycarbonyl, carboxyl, amino, mono- or di-alkylamino, or amido, each optionally substituted;

each $R^8$ is independently H, or alkyl, hydroxyl, alkoxy, halo, cyano, nitro, mercapto, thioalkoxy, alkoxycarbonyl, carboxyl, amino, mono- or di-alkylamino, or amido, each optionally substituted;

each n is independently 1, 2, 3 or 4;

and pharmaceutically acceptable salts, solvate, or hydrate thereof;

wherein said composition comprimises at least one of the group consisting of sodium carboxymethylcelluose, propylene glycol, polyethylene glycol, and sodium lauryl sulfate.

2. The pharmaceutical composition of claim 1, wherein the compound of Formula I is any of Compounds 1-2 in the table below:

| Cmpd No. | $R^1$ | $R^2$ | $R^3$ | $R^4$ | $R^5$ | $R^6$ |
|---|---|---|---|---|---|---|
| 1 | i-Pr | Me | Me | $CH_3CH(OH)—$ | i-Bu | Et |
| 2 | i-Pr | H | Me | $CH_3CH(OH)—$ | i-Bu | Et. |

3. The pharmaceutical composition of claim 2 further comprising an additional therapeutic agent.

4. The pharmaceutical composition of claim 3 wherein the additional therapeutic agent is an anti-cancer agent, chemotherapeutic agent, an anti-angiogenesis agent, cytotoxic agent, or an anti-proliferation agent.

5. A kit comprising an effective amount of the composition of claim 1, in unit dosage form, together with instructions for administering the composition to a subject suffering from or susceptible to a cell proliferation disorder.

* * * * *